United States Patent
Stamas et al.

(10) Patent No.: US 8,257,667 B2
(45) Date of Patent: Sep. 4, 2012

(54) CYTOCENTRIFUGE SAMPLE CONTAINER HOLDER AND SUPPORT DEVICE

(75) Inventors: Christopher Stamas, Wellesley, MA (US); Michael Faulkner, Leominster, MA (US)

(73) Assignee: Biomedical Polymers, Inc., Gardner, MA (US)

( * ) Notice: Subject to any disclaimer, the term of this patent is extended or adjusted under 35 U.S.C. 154(b) by 314 days.

(21) Appl. No.: 12/584,932

(22) Filed: Sep. 15, 2009

(65) Prior Publication Data
US 2011/0064629 A1    Mar. 17, 2011

(51) Int. Cl.
*B04B 1/00*    (2006.01)
(52) U.S. Cl. ........ 422/548; 422/500; 422/560; 422/561; 422/547; 422/506
(58) Field of Classification Search ............... 422/72, 422/500–502, 560–561, 547–548, 506
See application file for complete search history.

(56) References Cited

U.S. PATENT DOCUMENTS

| | | | |
|---|---|---|---|
| 3,552,846 A * | 1/1971 | Hansen | ............ 353/103 |
| 4,209,923 A | 7/1980 | Wendt | |
| 4,678,579 A | 7/1987 | Griffin | |
| 4,853,188 A * | 8/1989 | Toya | ............ 427/2.11 |
| 5,392,913 A | 2/1995 | Merrick | |
| 5,480,484 A | 1/1996 | Kelley et al. | |
| 5,589,400 A | 12/1996 | Hayes | |
| 5,679,154 A | 10/1997 | Kelley et al. | |
| 6,162,401 A | 12/2000 | Callaghan | |
| 7,297,550 B2 | 11/2007 | Cortelazzo | |
| 7,575,719 B2 | 8/2009 | Lomas | |
| 7,628,955 B2 * | 12/2009 | Kerrod et al. | ............ 422/72 |
| 2006/0135337 A1 | 6/2006 | Kerrod et al. | |

OTHER PUBLICATIONS

Thermo Electron Corporation, "Shandon Cytospin® Cytocentrifuge, Thin-Layer Cell Preparation System," Product Brochure, 2004, pp. 1-8.

* cited by examiner

*Primary Examiner* — Jyoti Nagpaul
(74) *Attorney, Agent, or Firm* — Iandiorio Teska & Coleman, LLP

(57) ABSTRACT

A support device for a cytocentrifuge sample container includes a support body including spaced edge fingers and a clip hinged to the support body. The clip has a latch for each spaced edge finger of the support body and edge members each including lugs engaging slotted ledges in the sample container.

22 Claims, 7 Drawing Sheets

CYTOCENTRIFUGE SAMPLE CONTAINER HOLDER AND SUPPORT DEVICE

FIELD OF THE INVENTION

The subject invention relates to cytocentrifuge sample containers, and holders or clips for the same.

BACKGROUND OF THE INVENTION

A plastic cytology funnel along with a filter card and slide are typically retained together via a metal clip style holder itself configured to be placed in a cytocentrifuge. See U.S. Pat. No. 5,589,400 incorporated herein by this reference.

U.S. Pat. No. 7,297,550, also incorporated herein by this reference, discloses a plastic holder with mutually opposite hook-shaped tabs sized to retain the slide, filter card, and funnel base.

Thermo Shandon Scientific Ltd. also offers for sale a plastic "EZ" funnel with a plastic holder hinged to one side. Again, a hook-shaped tab on the holder engages the front of the funnel base. The customer must purchase both the funnel and the holder from the same company.

Accordingly, there is a need for a new source of cytofunnel sample container holders which are not attached to the funnel at the time of purchase.

BRIEF SUMMARY OF THE INVENTION

The subject invention features a new cytocentrifuge sample container holder/support device.

The subject invention features a support device for a cytocentrifuge sample container. One preferred device comprises a support body including spaced edge fingers and a clip hinged to the support body. The clip includes a latch for each spaced edge finger of the support body and edge members each including lugs engaging slotted ledged in the sample container.

In one preferred embodiment, the support body and the clip are made of plastic and the clip is configured as a frame with top and bottom members connected to the edge members. The clip is typically hinged at its bottom member to the bottom of the support body. A latch extends rearwardly from each edge member of the clip. Each lug preferably includes a generally convex member rearwardly extending from an edge member. The support body may further include opposite edge pivots, and spaced lower retainer tabs. The clip may be hinged at its bottom to a bottom portion of the support body via a flexible hinge. The flexible hinge may include an opening and a catch member frictionally received in the opening when the clip is pivoted towards the support body. The support body may also include spaced edge walls and an edge finger located outwardly on each side wall. Each edge finger preferably extends at an angle upwardly and then terminates at a horizontal portion.

One support device for a cytocentrifuge sample container in accordance with the subject invention includes a support body including at least a first edge latch mechanism, a clip hinged to the support body and including at least a second latch mechanism cooperating with the first latch mechanism to releasably secure the clip adjacent the body, and means for biasing the clip with respect to the support body when a sample container, slide, and filter card are positioned between the support body and the clip. The means for biasing the clip with respect to the support body may include edge lugs extending outwardly from the clip. One support device in accordance with the subject invention features a plastic support body, a plastic clip configured as a frame with spaced edge members interconnected via spaced top and bottom members, a living plastic hinge interconnecting the clip bottom member with the support body, at least a first latch mechanism associated with one edge member of the clip, and at least a second latch mechanism associated with the support body and cooperating with the first latch mechanism.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
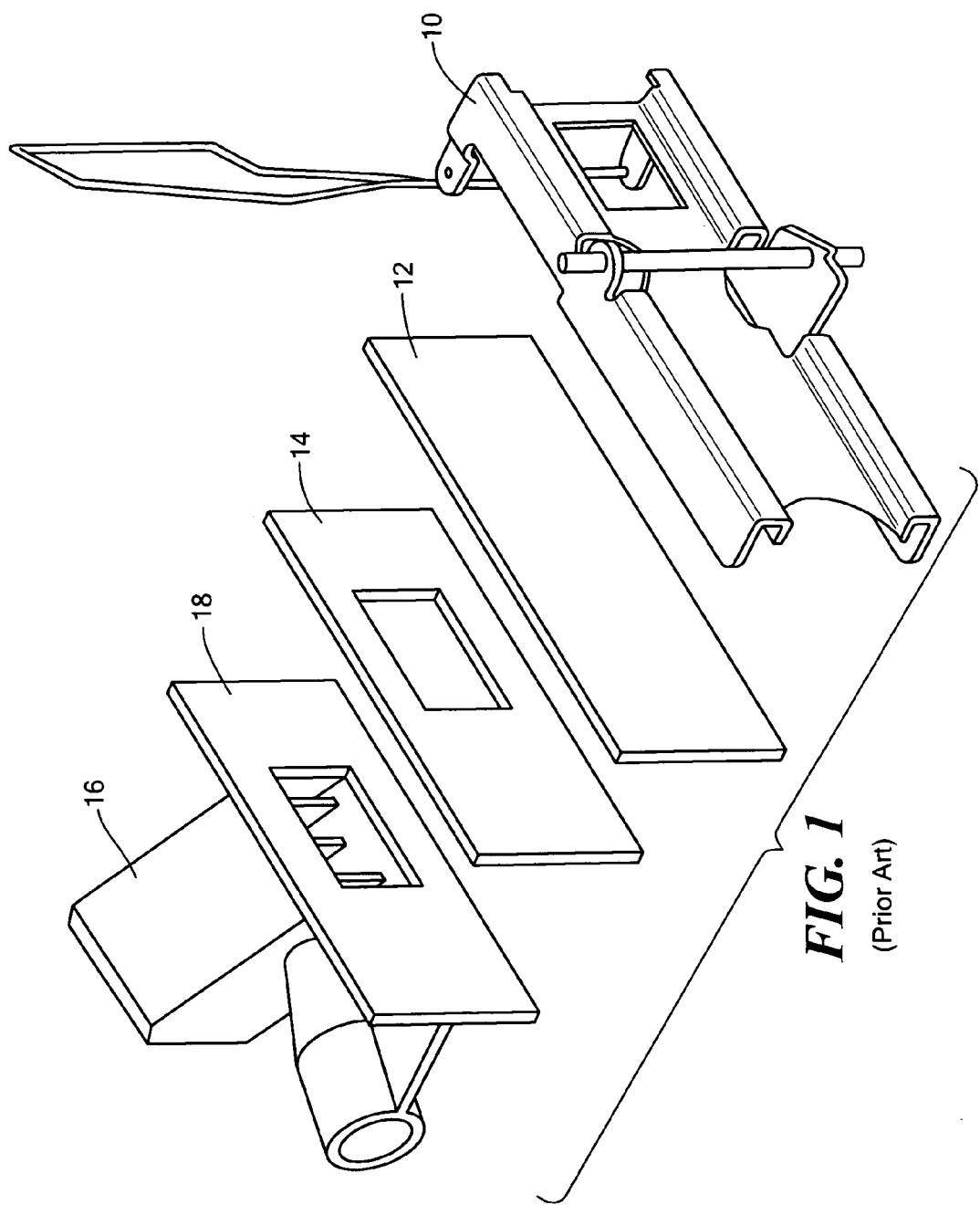
FIG. 1 is a schematic three-dimensional exploded view of a prior art metal clip style holder used in conjunction with a slide, filter card, and sample container.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 2:
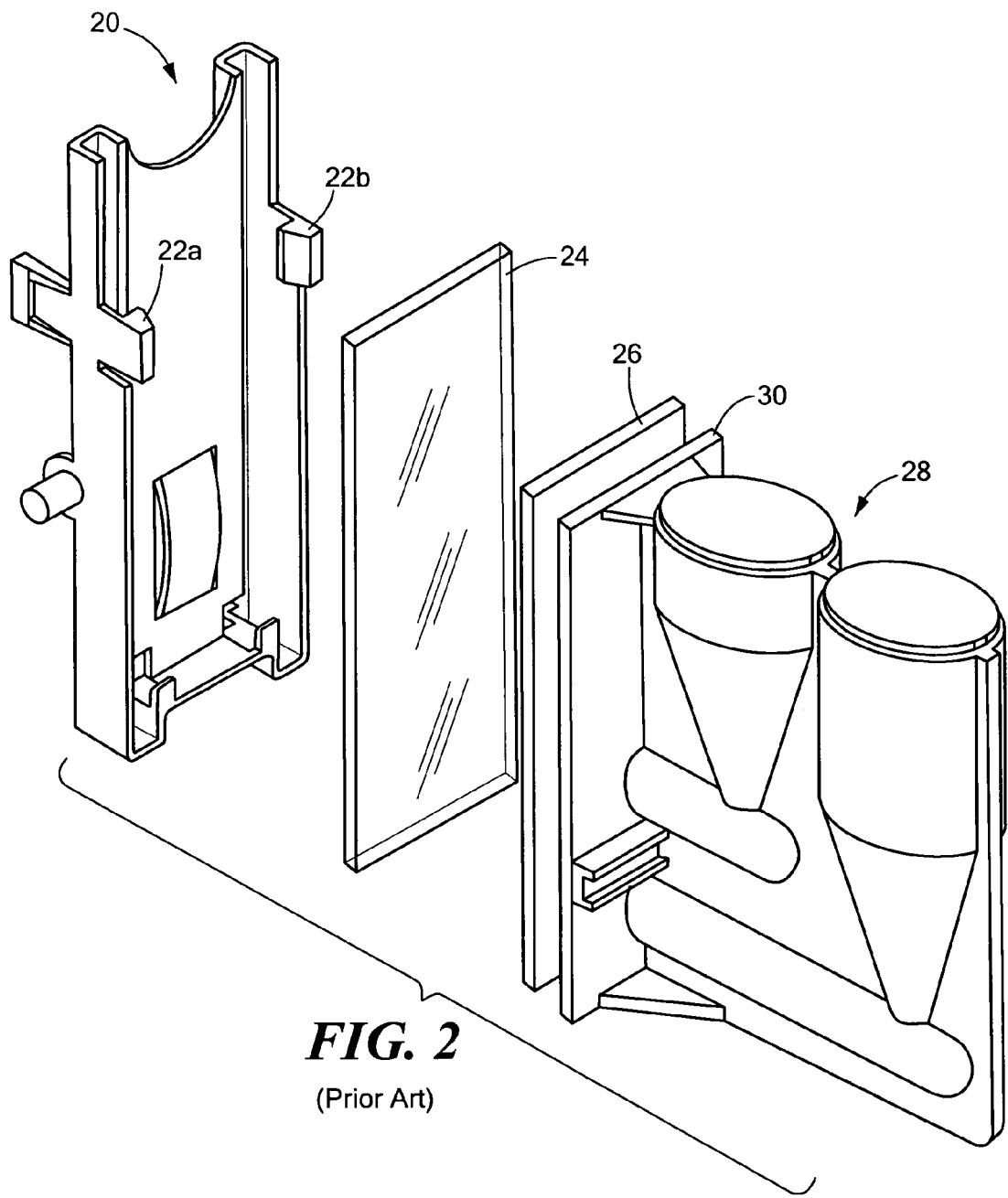
FIG. 2 is a schematic three-dimensional exploded view showing another prior art holder for a slide, filter card, and sample container.
Figure 3:
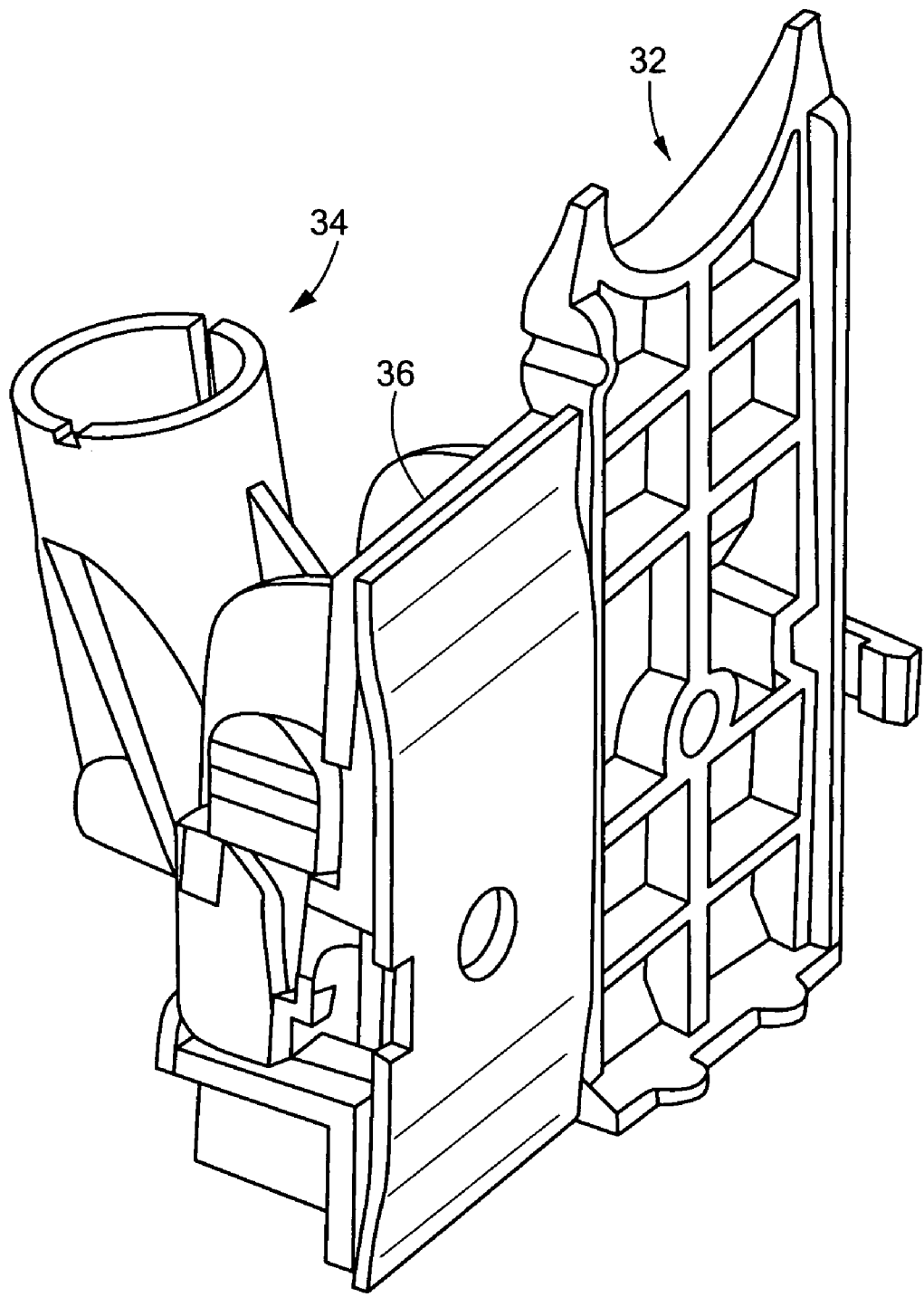
FIG. 3 is a schematic three-dimensional rear view showing still another prior art holder integral with the sample container.

FIG. 1 shows prior art metal clip style support 10 for retaining, in succession, slide 12, filter card 14, and sample container 16 base 18. See U.S. Pat. No. 5,589,400. FIG. 2 shows prior art plastic support 20 with hook-shaped edge wall tabs 22a and 22b for retaining, in succession, slide 24, filter card 26, and sample container base 30. See U.S. Pat. No. 7,297,550. FIG. 3 shows plastic holder 32 hinged to one side of sample container 34 base 36.

As noted in the background section above, there is a need for a different source of supply of supports or holders for cytocentrifuge sample containers, slides, and filter cards.

Figure 4:
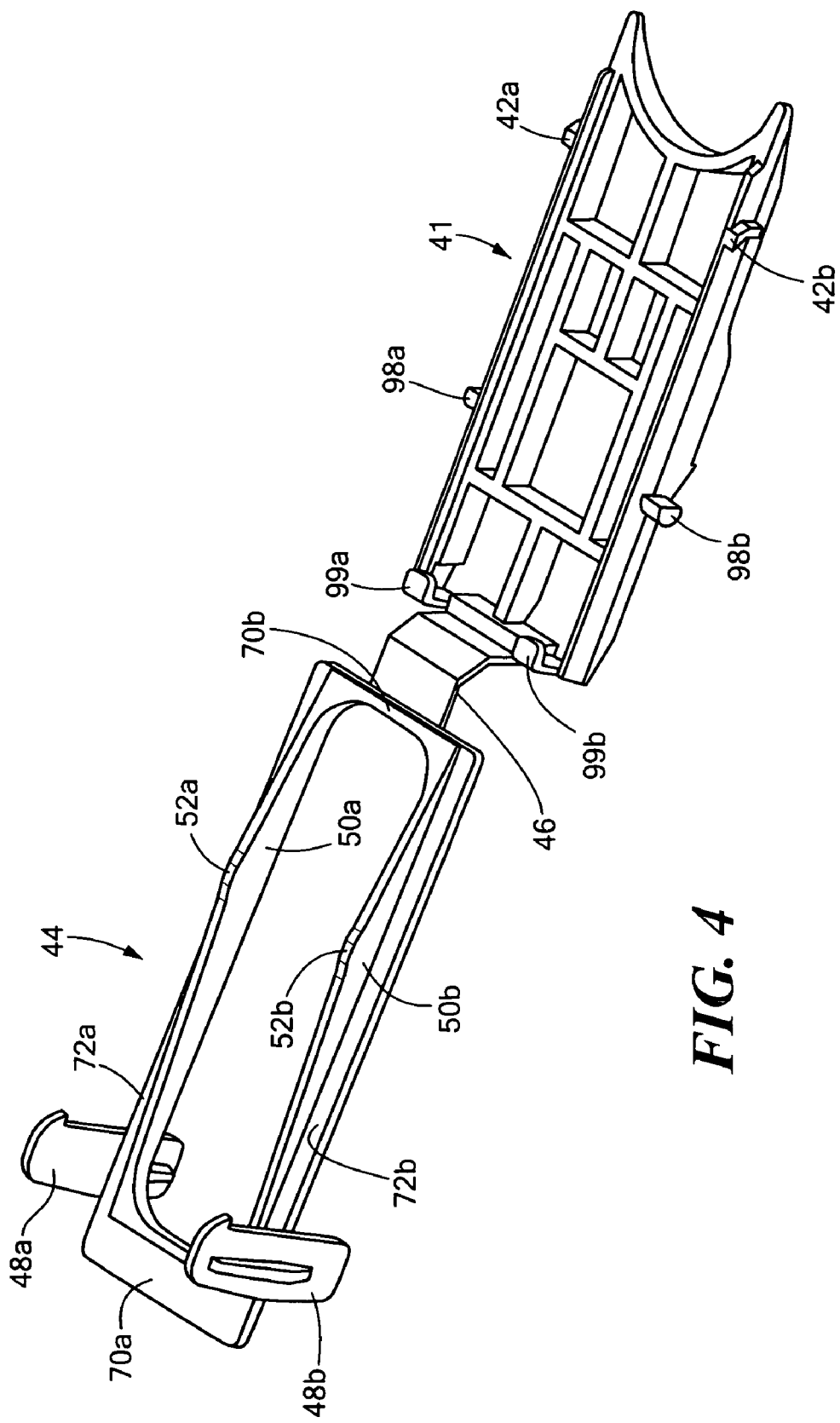
FIG. 4 is a schematic three-dimensional top view showing an example of a support device for a cytocentrifuge sample container in accordance with the subject invention.
Figure 5:
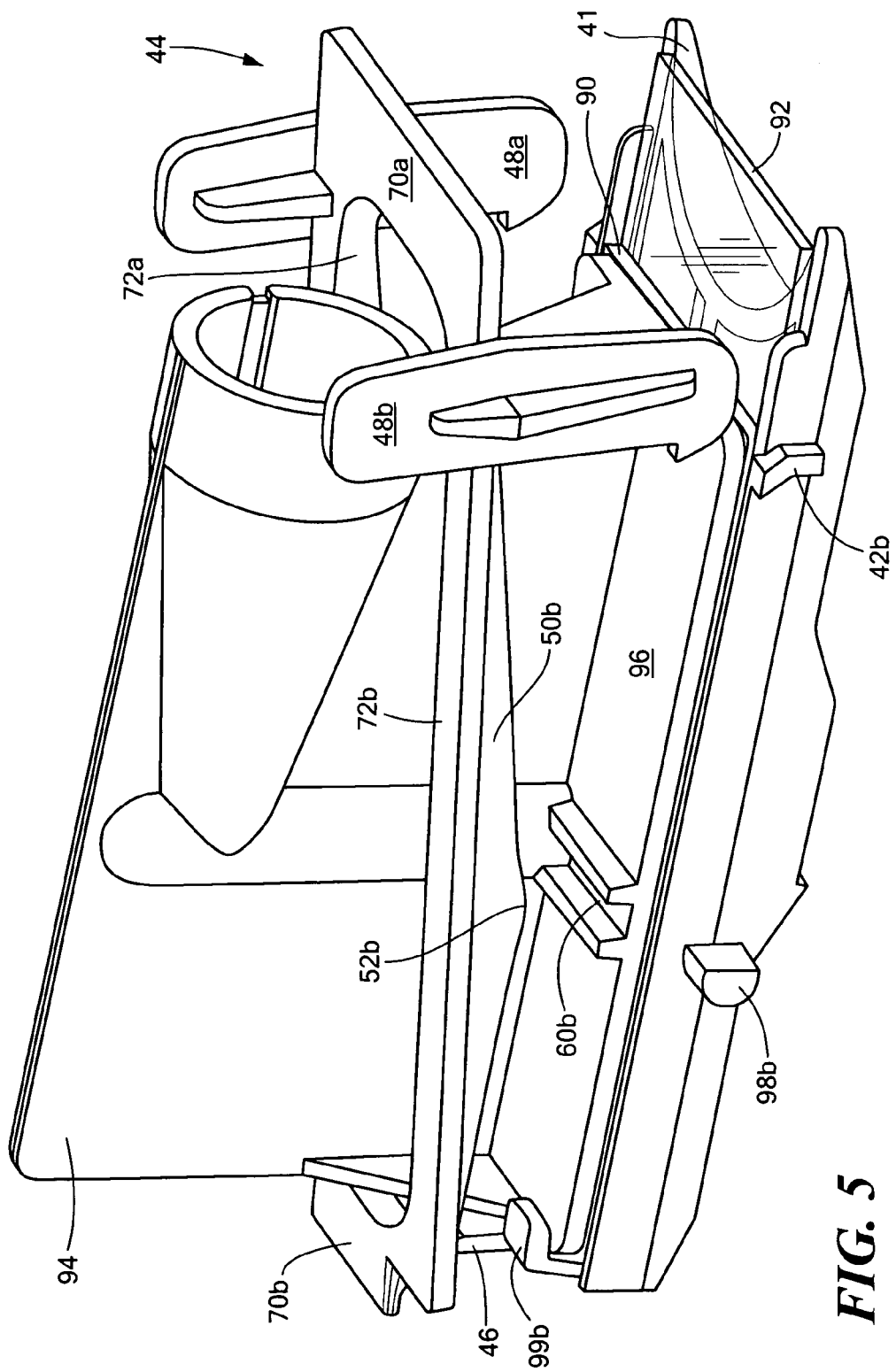
FIG. 5 is a schematic three-dimensional side view showing the support device of FIG. 4 with a sample container, slide, and filter card in place between the clip and the support body just prior to engaging the clip with the support body.
Figure 6:
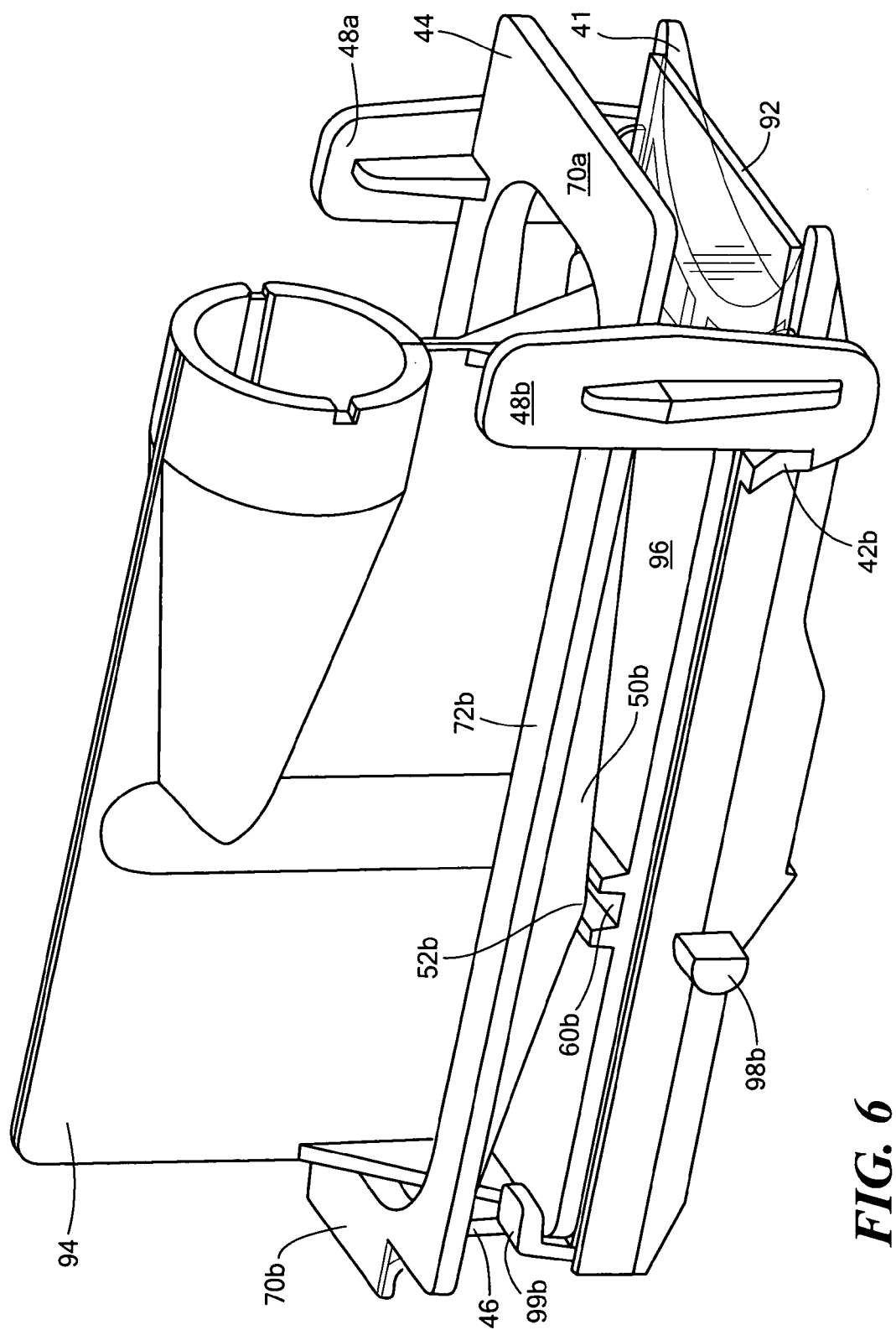
FIG. 6 is a schematic three-dimensional side view, showing the clip of FIG. 5 now engaged with the holder support body.

In one preferred embodiment, support or holder 40, FIGS. 4-6 in accordance with the subject invention includes support body 41 with edge or side fingers 42a and 42b. Clip 44 is hinged, via living hinge 46, to support body 41. Clip 44 edge latches 48a and 48b cooperate with edge fingers 42a and 42b, respectively, to releasably secure clip 44 to support body 41. The result is a more positive engagement of clip 44 to support body 41. Edge members 50a and 50b of clip 44 include lugs 52a and 52b engaging slotted ledges (see, for example, ledge 60b, FIGS. 5-6) associated with the front of the sample container base. Preferably, body 41, clip 44, and hinge 46 are made of plastic and molded in an integral fashion.

FIGS. 4-6 show how clip 44 is preferably configured as a frame with spaced top and bottom members 70a and 70b connected via spaced edge or side members 72a and 72b. Hinge 46 interconnects bottom member 70b of clip 44 with the bottom of support body 41. Latches 48a and 48b extend rearwardly from edge members 72a and 72b, respectively. Lugs 50a and 50b are generally convex members extending rearwardly from edge members 72a and 72b, respectively. They serve to exert pressure on filter card 90, FIGS. 5-6 and slide 92 when positioned between clip 44 and support body 41 along with sample container 94 base 96. Support body edge pivots 98a and 98b are included for mounted the assembly in a cytocentrifuge. Support body 41 typically also includes spaced lower retainer tabs 99a and 99b. FIGS. 5-6 shows sample container 94 base 96 retained by clip 44 against filter card 90, slide 92, and support body 41.

The design of sample container may vary. Also, latch mechanisms other than those shown may be used. It is possible, for example, for latches 48a and 48b to reside on body 41 and fingers 42a and 42b to reside on clip 44.

The subject invention, in the preferred embodiment, features several ways to bias the clip 44 with respect to base support 41 and slide 92, filter 90, and container base 96 between clip 44 and support body 41. For example, lug members 52a and 52b are sized along with the latches 48a and 48b to press on sample container 94 base 96 when slide 92 and filter card 90 are in position between clip 44 and support 41. Also, the frame-like structure of clip 44 helps ensure all of the components are secured tightly together. As clip 44, FIG. 5 is pivoted to be releasably locked with respect to base 41 as shown in FIG. 5, lugs 52a exert pressure on the front of container 94 base 96 and then latches 48a and 48b lock onto fingers 42a and 42b as shown in FIG. 6. Fingers 80a and 80b, FIG. 4 press on slide 92, FIGS. 5-6 keeping it pressed against filter card 90.

Figure 7:
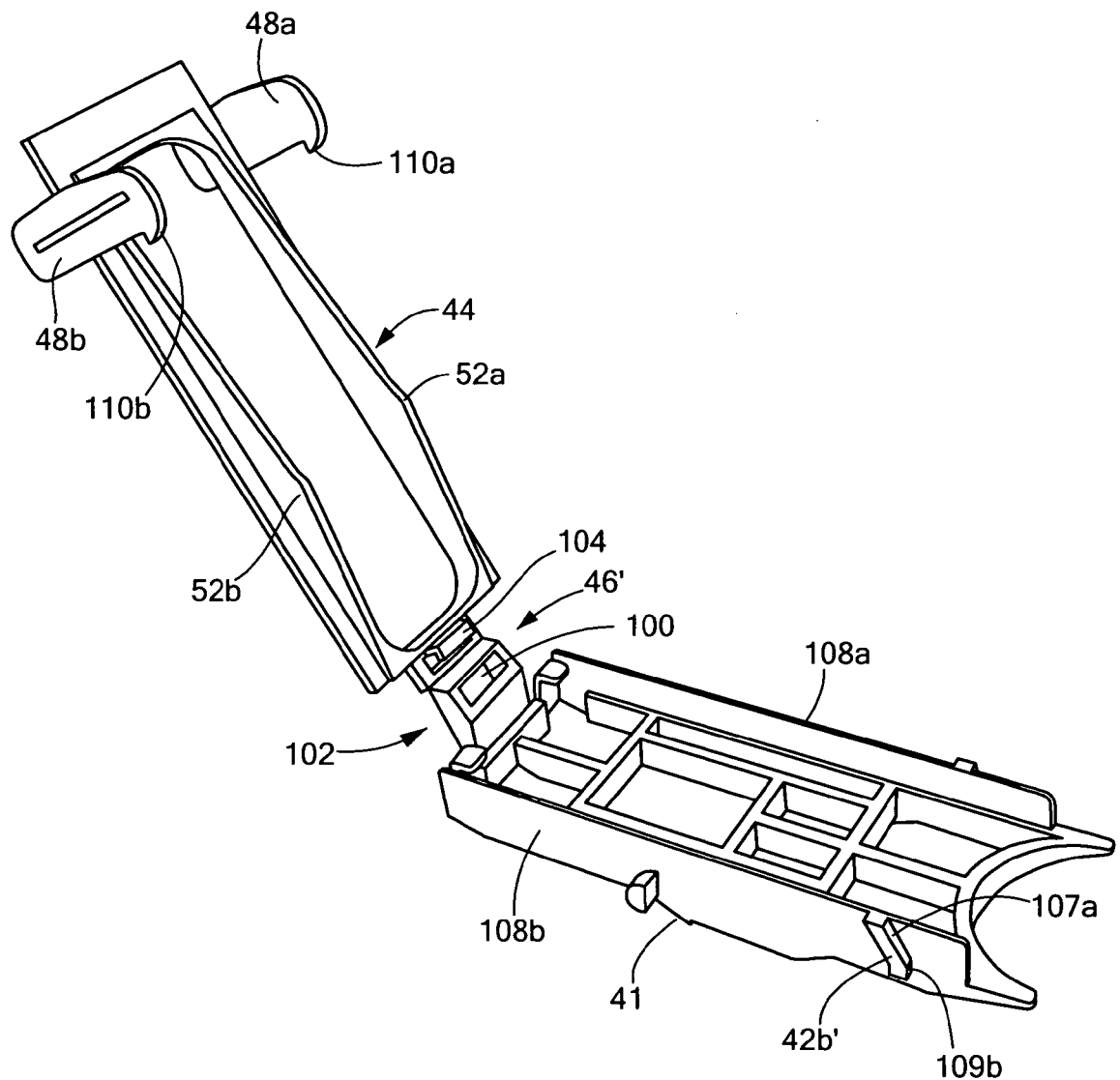
FIG. 7 is a schematic three-dimensional view showing another version of a support device in accordance with the invention.

FIG. 7 shows another design where living plastic flexible hinge 46' includes opening 100 on one side of pivot portion 102 and catch member 104 on the other side of pivot portion 102. Catch member 104 is frictionally received in opening 100 when clip 44 is pivoted towards support body 41. This configuration prevents twisting of clip 44 and helps ensure latches 48a and 48b are properly aligned to engage fingers 42a' and 42b', respectively, when clip 44 is pivoted towards support body 41. Also, in this version, support body 41 includes spaced edge walls 108a and 108b and, as shown for edge finger 42b', each edge finger extends at an angle upwardly as shown at 107a and then terminates at a horizontal portion 109a. In this way, the distal hook shaped portion 110b of latch 48b rides up on upwardly angled portion 107a and then reliably locks over horizontal portion 109b.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A support device for a cytocentrifuge sample container, the device comprising:
    a support body including spaced edge fingers;
    a clip hinged to the support body, said clip configured as a frame and including:
        a latch for each spaced edge finger of the support body,
        edge members each including lugs engaging slotted ledges in the sample container, and
        top and bottom members connected to the edge members.

2. The device of claim 1 in which the support body and the clip are made of plastic.

3. The device of claim 1 in which the clip is hinged at its bottom member to the bottom of the support body.

4. The device of claim 1 in which a latch extends rearwardly from each edge member of the clip.

5. The device of claim 1 in which each lug includes a generally convex member rearwardly extending from an edge member.

6. The device of claim 1 in which the support body further includes opposite edge pivots.

7. The device of claim 1 in which the support body further includes spaced lower retainer tabs for engaging said sample container.

8. The device of claim 1 in which the clip is hinged at its bottom to a bottom portion of the support body via a flexible hinge.

9. The device of claim 8 in which the flexible hinge includes an opening and a catch member frictionally received in the opening when the clip is pivoted towards the support body.

10. The device of claim 1 in which the support body includes spaced edge walls and an edge finger is located outwardly on each side wall.

11. The device of claim 1 in which each edge finger extends at an angle upwardly and then terminating at a horizontal portion.

12. A support device for holding or supporting a separate cytocentrifuge sample container, the device comprising:
    a support body including at least a first edge latch mechanism;
    a clip hinged to the support body and including at least a second latch mechanism cooperating with the first latch mechanism to releasably secure the clip adjacent the support body; and
    means for biasing the clip with respect to the support body when a sample container, slide, and filter card are positioned between the support body and the clip.

13. The device of claim 12 in which the means for biasing the clip with respect to the support body includes edge lugs extending outwardly from the clip.

14. The device of claim 12 in which the clip is hinged at its bottom to a bottom portion of the support body via a flexible hinge.

15. The device of claim 14 in which the flexible hinge includes an opening and a catch member frictionally received in the opening when the clip is pivoted towards the support body.

16. A support device for holding or supporting a separate cytocentrifuge sample container, the device comprising:
    a plastic support body;
    a plastic clip configured as a frame with spaced edge members interconnected via spaced top and bottom members;
    a living plastic hinge interconnecting the clip bottom member with the support body;
    at least a first latch mechanism associated with one edge member of the clip; and
    at least a second latch mechanism associated with the support body and cooperating with the first latch mechanism.

17. The support device of claim 16 further including means for biasing the clip with respect to the support body.

18. The device of claim 17 in which the means for biasing the clip with respect to the support body includes a lug extending outwardly from each clip edge member.

19. The device of claim 16 in which the living plastic hinge includes an opening and a catch member frictionally received in the opening when the clip is pivoted towards the support body.

20. A support device for a cytocentrifuge sample container, the device comprising:
    a support body including spaced edge fingers;
    a clip hinged to the support body and including:
        a latch for each spaced edge finger of the support body, and
        edge members each including lugs engaging slotted ledges in the sample container, in which the clip is hinged at its bottom member to the bottom of the support body.

21. A support device for a cytocentrifuge sample container, the device comprising:
    a support body including spaced edge fingers;
    a clip hinged to the support body and including:
        a latch for each spaced edge finger of the support body, and
        edge members each including lugs engaging slotted ledges in the sample container; and
    a latch extending rearwardly from each edge member of the clip.

22. A support device for a cytocentrifuge sample container, the device comprising:
    a support body including spaced edge fingers;
    a clip hinged to the support body and including:
        a latch for each spaced edge finger of the support body, and
        edge members each including lugs engaging slotted ledges in the sample container, in which the clip is hinged at its bottom to a bottom portion of the support body via a flexible hinge, the flexible hinge including an opening and a catch member frictionally received in the opening when the clip is pivoted towards the support body.

* * * * *